(12) United States Patent
Schlomka (10) Patent No.: US 7,590,215 B2
(45) Date of Patent: Sep. 15, 2009

(54) COHERENT-SCATTER COMPUTER TOMOGRAPH

(75) Inventor: Jens-Peter Schlomka, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 244 days.

(21) Appl. No.: 11/569,806

(22) PCT Filed: Jun. 1, 2005

(86) PCT No.: PCT/IB2005/051786

§ 371 (c)(1),
(2), (4) Date: Nov. 30, 2006

(87) PCT Pub. No.: WO2005/120354

PCT Pub. Date: Dec. 22, 2005

(65) Prior Publication Data

US 2008/0285706 A1 Nov. 20, 2008

(30) Foreign Application Priority Data

Jun. 7, 2004 (EP) .................................. 0410568

(51) Int. Cl.
*A61B 6/00* (2006.01)
(52) U.S. Cl. .............................................. 378/4; 378/5
(58) Field of Classification Search .................... 378/4, 378/5
See application file for complete search history.

(56) References Cited

U.S. PATENT DOCUMENTS

| 4,751,722 | A | * | 6/1988 | Harding et al. | 378/6 |
|---|---|---|---|---|---|
| 5,231,652 | A | * | 7/1993 | Harding | 378/86 |
| 5,265,144 | A | * | 11/1993 | Harding et al. | 378/86 |
| 5,642,393 | A | | 6/1997 | Krug et al. | |
| 6,175,117 | B1 | * | 1/2001 | Komardin et al. | 250/363.06 |
| 6,445,761 | B1 | | 9/2002 | Myazaki et al. | |
| 6,470,067 | B1 | * | 10/2002 | Harding | 378/19 |
| 6,953,935 | B1 | * | 10/2005 | Hoffman | 250/370.13 |
| 7,065,175 | B2 | * | 6/2006 | Green | 378/57 |
| 7,092,485 | B2 | * | 8/2006 | Kravis | 378/57 |
| 7,283,613 | B2 | * | 10/2007 | Harding | 378/86 |
| 2002/0150202 | A1 | | 10/2002 | Harding et al. | |
| 2003/0210761 | A1 | | 11/2003 | Hoffman | |

(Continued)

FOREIGN PATENT DOCUMENTS

DE 10009285 A1 8/2001

(Continued)

OTHER PUBLICATIONS

Saoudi et al., A Novel APD-Based Detector Module for Multi-Modality PET/SPECT/CT Scanners, IEEE Transactions on Nuclear Science, vol. 46, No. 3, Jun. 1999, pp. 479-484.*

(Continued)

*Primary Examiner*—Edward J Glick
*Assistant Examiner*—Alexander H Taningco (57) ABSTRACT

Conventional CSCT may require a complex reconstruction involving a large number of calculations. According to an exemplary embodiment of the present invention, additional collimators are used in combination with energy revolving detectors, which may allow that a CSCT image may be reconstructed by a simple superposition of images obtained from different viewing angles in a direct tomography data acquisition scheme. Advantageously, a reconstruction may be avoided. Advantageously, this may allow for an improved image quality while reducing an amount of calculations required for generating the output image.

23 Claims, 4 Drawing Sheets

U.S. PATENT DOCUMENTS

2004/0079232 A1  4/2004  Groh et al.

FOREIGN PATENT DOCUMENTS

EP  1062914 A1  12/2000

OTHER PUBLICATIONS

Harding, X-ray Scatter Tomography for Explosive Detection, Radiation Physics and Chemistry, 71, 2004, pp. 869-881.*

Stefan M. Schneider, et al: Coherent Scatter Computed Tomography Applying a Fan-Beam Geometry, Proc. SPIE vol. 4320, 2001, pp. 754-763.

G. Harding, et al: Energy-Dispersive X-Ray Diffraction Tomography, vol. 35, No. 1, Jan. 1990, pp. 33-41, XP000101065.

Written Opinion of the International Searching Authority PCT/IB2005/051786.

* cited by examiner

COHERENT-SCATTER COMPUTER TOMOGRAPH

The present invention relates to the field of coherent-scatter computer tomography (CSCT), where radiation such as x-rays is applied to an object of interest. In particular, the present invention relates to a computer tomography apparatus for examination of an object of interest, to a data processing device and to a method of performing a fan-beam coherent scatter computer tomography scan.

U.S. Pat. No. 4,751,722 describes a device based on the principle of registration of an angled distribution of coherent scatter radiation within angles of 1° to 12° as related to the direction of the beam at X-ray energies around 100 keV. As set forth in U.S. Pat. No. 4,751,722, the main fraction of elastic scattered radiation is concentrated within angles of less than 12° and the scattered radiation has a characteristic angle dependency with well marked maxima, the positions of which are determined by the irradiated substance itself. As the distribution of the intensity of the coherent scatter radiation in small angles depends on the molecular structure of the substance, different substances having equal absorption capacity (which cannot be differentiated with conventional transillumination or CT) can be distinguished according to the intensity of the angled scattering of coherent radiation typical for each substance.

Due to the improved capabilities of such systems to distinguish different object materials, such systems find more and more application in medical or in industrial fields.

The dominant component of low-angle scatter is coherent scatter. Because coherent scatter exhibits interference effects which depend on the atomic arrangement of the scattering sample, coherent scatter computer tomography (CSCT) is in principle a sensitive technique for imaging spatial variations in the molecular structure of tissues across a 2D object section.

Harding et al "Energy-dispersive x-ray diffraction tomography" Phys. Med. Biol., 1990, Vol. 35, No. 1, 33-41 describes an energy dispersive x-ray diffraction tomography (EXDT) which is a tomographic imaging technique based on an energy analysis at fixed angle, of coherent x-ray scatter excited in an object by polychromatic radiation.

According to this method, a radiation beam is created by the use of suitable aperture systems, which has the form of a pencil and thus is also referred to as a pencil beam. Opposite to the pencil beam structure, one detector element suitable for an energy analysis is arranged for detecting the pencil beam altered by the object of interest.

Due to the use of the pencil beam in combination with only one or a few detector elements, only a limited number of photons emitted by the source of radiation and thus only a reduced amount of information can be measured. In case EXDT is applied to larger objects, such as, for example, to pieces of baggage, EXDT has to be used in a scanning mode, thus causing extremely long measurement times.

A coherent scatter set-up applying a fan-beam primary fan and a 2-dimensional detector in combination with CT was described in U.S. Pat. No. 6,470,067 B1 thus overcoming the long measurement time involved in EXDT scanning mode. The shortcoming of the angle-dispersive set-up in combination with a polychromatic source are blurred scatter functions, which are described, for example, in Schneider et al. "Coherent Scatter Computed Tomography applying a Fan-Beam Geometry" Pro. SPIE, 2001, Vol. 4320 754-763.

Still, there is a need for fast coherent scatter CTs involving a reduced amount of mathematical operations.

It is an object of the present invention to provide for a fast coherent scatter computer tomography apparatus.

According to an exemplary embodiment of the present invention, a computer tomography apparatus for examination of an object of interest is provided, wherein the computer tomography apparatus comprises a source of radiation, a scatter radiation detector for receiving a scatter radiation scattered by the object of interest and a first collimator. The scatter radiation detector is arranged opposite to the source of radiation with an offset with respect to a fan plane, extending though the object of interest and the source of radiation. The scatter radiation detector has a plurality of regions. Each of the regions comprises at least one first detector element. The first detector elements are energy resolving detector elements. The first collimator is adapted such that radiation impinging on the at least one first detector element of a respective region of the plurality of regions is substantially restricted to radiation scattered from a predetermined section of the object of interest. The source of radiation is adapted such that a fan beam is applied to the object of interest in the fan plane.

To allow for the spatial assignment of the received scattered radiation, the first collimator is provided together with the energy resolving scatter radiation detector, ensuring that only scatter radiation having a predetermined angle with respect to the source of radiation and with respect to the object of interest impinges onto the respective detector element of the scatter radiation detector. Thus, the energy resolving detector, i.e. the scatter radiation detector, measures the energy distribution of the scatter radiation scattered from the predetermined section of the object of interest. The predetermined section is determined by the arrangement of the collimator, i.e. of the focus of the collimator. From this, an output image may be determined which has a spatial resolution. Advantageously, due to this arrangement, the readouts of the radiation detector may be composed to an output image without a lot of calculations, which may allow for a reduced processing time. Advantageously, a scatter distribution of the object of interest may be determined from only one projection, i.e. without a rotation of the gantry, which may allow for a very fast determination of the scatter distribution of the object.

According to another exemplary embodiment of the present invention, the first collimator comprises a second collimator and a third collimator. The second collimator is focused at the source of radiation, whereas the third collimator defines a distinct scatter angle and selects scattering from only a section of the object of interest. By arranging the first and second collimators in layers above the scatter radiation detector, or one after the other with respect to the source of radiation, the radiation impinging on the respective detector element of the scatter radiation detector may be restricted to radiation scattered in a predetermined small section or region of the object of interest. In other words, by applying the second and third collimators, the first collimator may be realized such that each detector element of the scatter radiation detector associated with the first collimator has a predetermined "line of vision" of the object of interest.

According to another exemplary embodiment of the present invention, the second and third collimators are realized by using lamellae, which are focused at the source of radiation for the second collimator and which are focused at the section of the object of interest such that the "view" of the respective detector elements associated with the respective portion of the first collimator have a predetermined line of vision.

According to another exemplary embodiment of the present invention, the second and third collimators are implemented by means of a slot collimator comprising holes which, for each respective region or for each respective detector element associated therewith are respectively focused at the source of radiation and the section of the object of interest. This may allow for a first collimator having a simple and robust arrangement.

According to another exemplary embodiment of the present invention, a primary radiation detector is provided in the central plane for receiving a primary radiation attenuated by the object of interest. Advantageously, this may allow to collect scatter radiation data and attenuation data at the same time, i.e. during the same scan, and to use the attenuation data for compensating the scatter radiation data. Advantageously, this may allow for very accurate scanning results.

According to another exemplary embodiment of the present invention, the energy resolving elements are direct converting semi-conductor cells and the primary radiation cells are scintillator cells.

According to another exemplary embodiment of the present invention, the computer tomography apparatus further comprises a calculation unit, which is adapted to generate a first output image without performing a reconstruction. According to another exemplary embodiment of the present invention, the calculation unit is further adapted to generate the first output image by superposing second images corresponding to readouts of the scatter radiation detector obtained from different viewing angles with respect to the object of interest.

In other words, due to the fact that the first collimator is adapted such that each region or each detector element of the radiation detector detects only radiation scattered from a relatively small section of the probe, the detector signals of the scatter radiation detector may simply be superposed for generating the output image. Advantageously, no CT-like reconstruction has to be performed, which may allow to further improve the processing speed, which overall reduces an amount of calculations required for generating the output image. In other words, by using the first collimator according to the present invention, with, for a example two-dimensional energy resolving scatter radiation detector, reconstruction is no longer necessary. Instead, the CSCT image may be determined from a simple superposition or overlaying of images obtained from different angles in a direct tomography data acquisition scheme. Advantageously, due to this a reconstruction may be avoided. Furthermore, advantageously, the present invention may be implemented using a common CT geometry. By doing so, CT data acquisition may be performed simultaneously with CSCT and an improved attenuation correction may be carried out. Furthermore, the two-dimensional collimators reduce multiple scattered background, and thus allow for an improved quality of the measured scatter function or of the output image.

This is further described in the exemplary embodiments where the calculation unit of the computer tomography apparatus is further adapted to superimpose images of different viewing angles and where at least one of an attenuation correction and a primary radiation intensity correction may be performed.

According to another exemplary embodiment of the present invention, a data processing device is provided, comprising a memory for storing the readouts from the scatter radiation detector of a computer tomography apparatus having the arrangement according to the present invention and a processor, which is adapted for generating a first output image from the readouts without performing a reconstruction.

Advantageously, due to the fact that no reconstruction has to be performed, an amount of calculations may be reduced, which allows to have a data processing device without a high performance processor. For example, the data processing device may be implemented by means of a workstation or a personal computer having interfaces to acquire or read-in the readouts of the radiation detector.

According to further exemplary embodiments of the data processing device, the processor is further adapted to generate the output image by superimposing images from different viewing angles and an attenuation correction or a primary radiation intensity correction may be performed. Advantageously, this may allow for an improved quality of the measured scatter function.

According to another exemplary embodiment of the present invention, a method of performing a fan beam coherent scatter computer tomography scan is provided, where a first output image is generated from readouts of a scatter radiation detector without performing a reconstruction. According to an aspect of this exemplary embodiment of the present invention, this may be achieved due to the provision of the collimator, which may provide for the spatial resolution by focusing the radiation, such that radiation impinging on at least one detector element of a respective region of the scatter radiation detector is substantially restricted to radiation scattered from a predetermined section of the object of interest.

Further exemplary embodiments of the method of the present invention are provided below.

It may be seen as the gist of an exemplary embodiment of the present invention that a collimator is provided in combination with energy resolving detectors, which may allow to avoid a reconstruction for generating an output image. The collimator is adapted such that radiation impinging on a detector element of the scatter radiation detector is substantially restricted to radiation scattered from a predetermined section of the object of interest. Due to this, a CSCT image may simply be generated by a superposition of images obtained from different viewing angles in a direct tomography data acquisition scheme. This may be implemented by using a common CT geometry. By doing so, CT data acquisition may be performed simultaneously with CSCT, which may allow for an improved attenuation correction. Furthermore, the collimators may reduce multiple scattered background, and thus an improved quality of the measured scatter function or of the output image may be achieved.

These and other aspects of the present invention will become apparent from and elucidated with reference to the embodiments described hereinafter.

Exemplary embodiments of the present invention will be described in the following, with reference to the following drawings.

In the following description of FIGS. 1 to 7, the same reference numerals are used for the same or corresponding elements.

Figure 1:
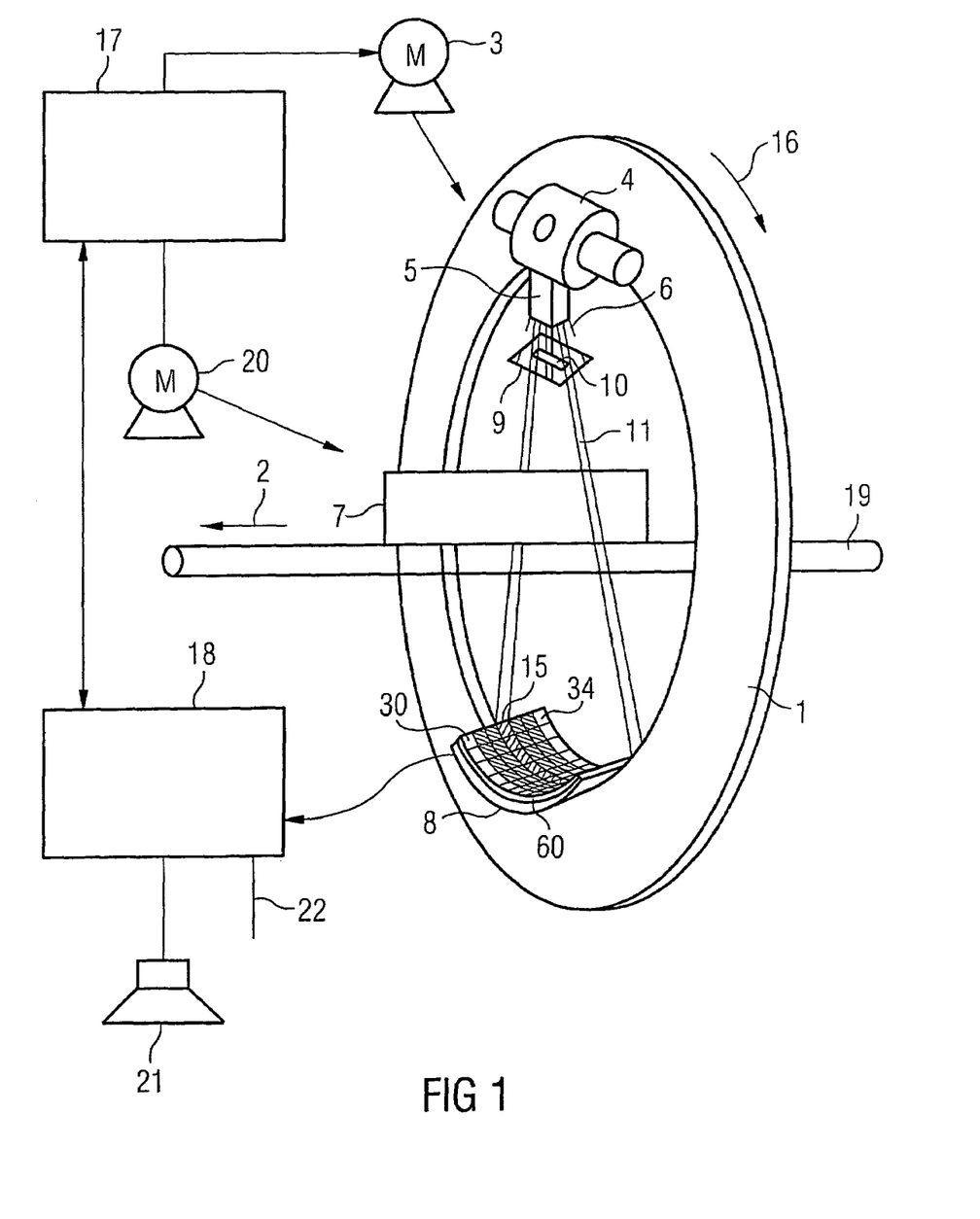
FIG. 1 shows a schematic representation of an exemplary embodiment of a coherent scatter computer tomograph according to the present invention.

FIG. 1 shows an exemplary embodiment of a coherent scatter computer tomography apparatus (CSCT) according to the present invention. With reference to this exemplary embodiment, the present invention will be described for the application in baggage inspection to detect hazardous materials such as explosives in items of baggage. However, it has to be noted that the present invention is not limited to applications in the field of baggage inspection, but can also be used in other industrial or medical applications, such as for example in bone imaging or a discrimination of tissue types in medical applications. Also, it should be noted that the present invention is not limited to scanners having a rotating gantry. It may also be applied to scanners with stationary gantry.

The computer tomograph depicted in FIG. 1, as already indicated above, is a fan-beam coherent scatter computed tomograph (CSCT), which allows, in combination with energy-resolving detectors and with a tomographic reconstruction, a good spectral resolution with a polychromatic cone-beam. The computer tomograph depicted in FIG. 1 comprises a gantry 1, which is rotatable around a rotational axis 2. The gantry 1 is driven by means of a motor 3. Reference character 4 designates a source of radiation, such as an x-ray source. Reference character 5 designates a first aperture system, which forms the radiation beam emitted from the radiation source 4 to a cone-shaped radiation beam 6. Furthermore, there is provided a second aperture system 9, consisting of a diaphragm or slit collimator. The aperture system 9 has the form of a slit 10, such that the radiation emitted from the source of radiation 4 is formed into a fan-beam 11. According to a variant of this exemplary embodiment of the present invention, the first aperture system 5 may also be omitted and only the second aperture system 9 may be provided.

The fan-beam 11 is directed such that it penetrates an item of baggage 7 arranged in the center of the gantry 1, i.e. in an examination region of the computer tomography and impinges onto collimator 60 which is arranged on detector 8. As may be taken from FIG. 1, the collimator 60 and the detector 8 are arranged on the gantry 1 opposite to the radiation source 4 such that the fan plane intersects the source of radiation 4 and the item of baggage 7 intersects a detector row or line preferably in the center of the detector 8. The detector 8 depicted in FIG. 1 has a plurality of detector lines, each comprising a plurality of detector elements. Due to the arrangement of the collimator in the detector in FIG. 1, the surface of the detector 8 is covered by the collimator 60 such that the arrangement of detector elements of the detector is covered in FIG. 1.

However, for a better understanding, the arrangement of detector lines of the detector 8 covered by the collimator 60 is indicated on the surface of the collimator 60.

The detector 8 comprises two types of radiation detector lines: a first type of detector lines 30 and 34, which are detector lines consisting of energy resolving detector cells. They are arranged such that they are outside of the surface of the detector 8 which is subjected to a direct illumination by the fan beam 11. According to an aspect of the present invention, these first detector elements (lines 30 and 34) are energy-resolving detector elements. Preferably, the energy resolving detector elements are direct-converting semiconductor detector cells. Direct-converting semiconductor detector cells directly convert the radiation into electrical charges—without scintillation. Preferably, these direct-converting semiconductor detectors have an energy resolution better than 20% FWHM, i.e. $\Delta E/E<0.2$, with $\Delta E$ being the Full-Width at Half Maximum (FWHM) of the energy resolution of the detector. The energy resolving detector elements may also be distributed in a non ordered fashion, i.e. not in lines.

Such detector cells of lines 30 and 34 may be cadmiumtelluride or CZT based detector cells, which are both outside of the fan plane of the fan-beam 11. In other words, all energy resolving lines 30 and 34 are arranged at the gantry 1 opposite to the x-ray source 4 with an offset from the fan plane in a direction parallel to the rotational axis 2. The detector lines 30 are arranged with a positive offset with respect to the direction of the rotational axis 2 depicted in FIG. 1, whereas the lines 34 are arranged with a negative offset from the central plane with respect to the direction of the rotational axis 2 depicted in FIG. 1. Also, as set forth above, the energy resolving detector elements are preferable arranged in regions of the detector 8 which are not subjected to direct illumination by the fan beam 11 such that they are adapted to measure the scatter radiation, i.e. the radiation scattered from the item of interest 7.

The detector lines 30 and 34 are arranged at the gantry 1 such that they are parallel to the fan plane with an offset in a positive or negative direction of the rotational axis 2 of the gantry 1, such that they receive or measure a scatter radiation scattered from the item of baggage 7 in the examination area of the computer tomograph. Thus, in the following, lines 30 and 34 will also be referred to as scatter radiation detector.

It has to be noted that instead of the provision of a plurality of energy resolving lines 30 and 34 on both sides of the fan plane, it may also be efficient to provide only a reduced number of lines on only one side of the fan plane.

Thus, if, in the following the term "scatter radiation detector" is used, it includes any detector with a 2-dimensional arrangement of energy resolving detector elements, which are arranged out of the fan plane of the fan-beam 11, such that they receive photons scattered from the item of baggage 7.

The second type of detector lines provided on the detector 8, are scintillator cells. In particular, line(s) 15 of scintillator cells is arranged on areas of the detector 8 which are subjected to direct illumination by the fan-beam 11. As indicated in FIG. 1 a line 15 may be arranged in a central area of the detector intersected by the fan plane. Line 15 may be parallel to the fan plane. In other words, line 15 is arranged for measuring the attenuation of the radiation emitted by the source of radiation caused by the item of baggage 7 in the examination region.

As already indicated with respect to the energy resolving lines 30 and 34, where the provision of only a few energy resolving line 30 or 34 may be sufficient, the provision of only a few lines 15 (or of only one line 15) measuring the attenuation caused by the item of baggage 7 of the primary beam of the fan-beam 11 in the fan plane may be sufficient. However, as in the case of the energy resolving lines 30 and 34, a provision of a plurality of detector lines 15, each comprising a plurality of scintillator cells, may further increase the measurement speed of the computer tomograph. In the following, the term "primary radiation detector" will be used to refer to a detector, including at least one scintillator cell or similar detector cells for measuring an attenuation of the primary radiation of the fan-beam 11.

Preferably, the detector cells of the detector 8 are arranged in lines and columns, wherein the columns are parallel to the rotational axis 2, whereas the lines are arranged in planes perpendicular to the rotational axis 2 and parallel to the fan plane of the fan-beam 11.

Furthermore, aperture systems (not shown in FIG. 1) may be provided to limit the dimensions of the fan-beam 11, such that no excess radiation is applied to the item of baggage 7, i.e. such that radiation not impinging onto the detector 8 may be cut away.

During a scan of the item of baggage 7, the radiation source 4 and the detector 8 are rotated along the gantry 1 in the direction indicated with arrow 16. For rotation of the gantry 1 with the source of radiation 4 and the detector 8, the motor 3 is connected to a motor control unit 17, which is connected to a calculation unit 18.

In FIG. 1, the item of baggage 7 is disposed on a conveyor belt 19. During the scan of the item of baggage 7, while the gantry 1 rotates around the item of baggage 7, the conveyor belt 19 may displace the item of baggage 7 along a direction parallel to the rotational axis 2 of the gantry 1. By this, the item of baggage 7 may be scanned along a helical scan path. However, the conveyor belt 19 may also be stopped during the scans to thereby measure single slices in a so-called "circular scan".

The detector 8 is connected to a calculation unit 18. The calculation unit 18 receives the detection results, i.e. the read-outs from the detector elements of the detector 8 and determines a scanning result on the basis of the scanning results from the detector 8, i.e. from the energy resolving lines 30 and 34 and the line 15 for measuring the attenuation of the primary radiation of the fan-beam. In addition to that, the calculation unit 18 communicates with the motor control unit 17 in order to coordinate the movement of the gantry 1 with the motors 3 and 20 or with the conveyor belt 19.

The calculation unit 18 may be adapted for reconstructing images from readouts of the primary radiation detector, i.e. detector line 15 and the scatter radiation detector, i.e. lines 30 and 34. The images generated by the calculation unit 18 may be output to a display (not shown in FIG. 1) via an interface 22.

Furthermore, the calculation unit 18 may be adapted for the detection of explosives in the item of baggage 7 on the basis of the readouts of the lines 30 and 34 and 15. This may be made automatically by calculating scatter functions from the readouts of these detector lines and comparing them to tables including characteristic measurement values of explosives determined during preceding measurements. In case the calculation unit 18 determines that the measurement values read out from the detector 8 match with characteristic measurement values of an explosive, the calculation unit 18 may automatically output an alarm via a loudspeaker 21.

As indicated above, reference numeral 60 in FIG. 1 designates a collimator. The collimator is arranged above the detector elements of the detector 8. The collimator 60 is arranged such that each detector element detects only radiation from a section of the item of baggage 7 having the form of a ray. This ray is determined from a cross-section of the illuminated volume of the item of baggage 7 and by the section of the item of baggage 7 seen by the respective detector element. In other words, the collimator 60, which may be a 2-dimensional collimator, as depicted in FIG. 1, ensures that only scatter radiation having a predetermined angle may be detected by the detector. In other words, the collimator 60 may be adapted such that radiation impinging onto a detector element of one of the energy resolving detector elements is substantially restricted to radiation scattered from a predetermined section of the item of baggage 7. Due to the fact that it is known which detector element looks at which section of the item of baggage 7, the energy distribution measured by the respective energy resolving detector element may be assigned to a predetermined coordinate in the item of baggage 7. Thus, the energy resolving detector measures the energy distribution of the scatter radiation from the predetermined section of the item of baggage 7 at a predetermined line of vision. From this, a coherent scatter function having a spatial resolution or an output image may be determined by the calculation unit 18. This will be described in further detail with reference to FIGS. 2-6.

Figure 2:
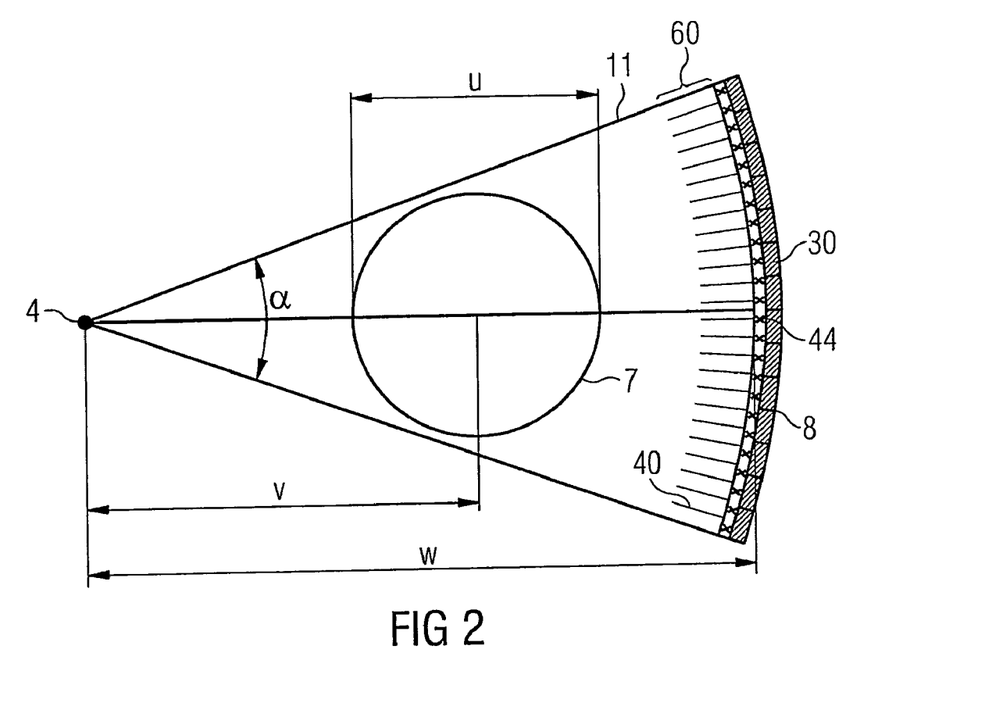
FIG. 2 shows a schematic representation of the geometry of the computer tomograph of FIG. 1 for the measurement of coherent scatter radiation.

FIG. 2 shows a simplified schematic representation of a geometry of the CSCT scanning system depicted in FIG. 1. As may be taken from FIG. 2, the x-ray source 4 emits the fan-beam 11 such that it includes the item of baggage 7 in this case having a diameter of u and covers the entire detector 8. The diameter of the object region may, for example, be 100 cm. In this case, an angle $\alpha$ of the fan-beam 11 may be 80°. In such an arrangement, a distance v from the x-ray source 4 to the center of the object region is approximately 80 cm and the distance of the detector 8, i.e. of the individual detector cells from the x-ray source 4 is approximately w=150 cm.

Since FIG. 2 shows a top-view onto this fan plane of fan-beam 11, it cannot be seen that the fan-beam 11 intersects the primary radiation detector, including line 15. However, as may be taken from FIG. 2, the collimator 60, including first lamellae 40 and second lamellae 44 may be distinguished, which are arranged in front of the detector lines 30 (or 34), i.e. in front of the scatter radiation detector of detector 8. As may be taken from FIG. 2, the lamellae 40 may be arranged such that they extend essentially perpendicular to the fan plane of the fan-beam 11. Essentially, the lamellae 44 may be arranged almost parallel to the fan-plane, the deviation from the parallel direction is the scatter angle. According to this exemplary embodiment, the lamellae 40 and 44 may form the collimator 60.

The lamellae 40 and 44 may be provided to avoid that the cells or lines of the detector 8 measure unwanted radiation having a different angle to the one desired. The lamellae 40 or 44 may have the form of blades, which can be respectively focused towards the source of radiation 4 or the item of baggage 7. The spacing of the lamellae can be chosen independently of the spacing of the detector elements.

Preferably, the first lamellae 40 are focused at the source of radiation, whereas the second lamellae 44 are focused at the object of interest. However, as will be described with reference to FIGS. 4 and 5, also the lamellae 44 may be arranged such that they are focused at the item of baggage 7, i.e. at predetermined sections of the item of baggage 7 and the lamellae 44 will be arranged such that they are focused at the source of radiation 4. In other words, it may be of no importance which one of the first and second collimators, including lamellae 40 and 44 is focused at the source of radiation or the item of baggage.

However, due to the different focus of the respective lamellae 40 and 44 it may be ensured that only radiation having a fixed predetermined angle impinges onto the detector and that each detector element only detects the scatter radiation from a predetermined oblong section of the item of baggage 7. This will be described in further detail with reference to FIGS. 4 and 5.

Figure 3:
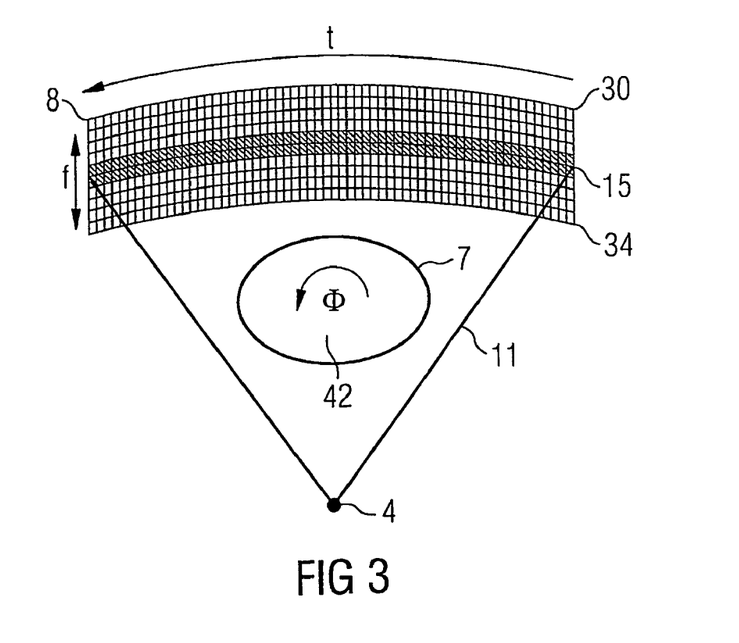
FIG. 3 shows another schematic representation of the geometry of the computer tomograph of FIG. 1.

FIG. 3 shows another schematic representation of a detector geometry as used in the computer tomograph of FIG. 1. However, no collimator 60 is shown for further explaining the arrangement of the detector 8. As already described with reference to FIG. 1, the detector 8 may comprise a plurality of energy resolving detector lines 30 and 34 and a plurality of lines 15 for measuring the attenuation of the primary fan-beam 11 caused by the item of baggage 7. As may be taken from FIG. 3, preferably the detector 8 is arranged such that a central line of lines 15 is intersected and parallel to the fan plane of the fan-beam 11 and thereby measures the attenuation of the primary radiation. As indicated by arrow 42, the radiation source of x-ray source 4 and the detector 8 may be rotated together around the item of baggage 7 to acquire projections from different angles. As depicted in FIG. 3, the detector 8 comprises a plurality of columns t and lines f.

Instead of a bent detector 8, as depicted in FIGS. 1, 2 and 3, it is also possible to use a flat detector array.

Figure 4:
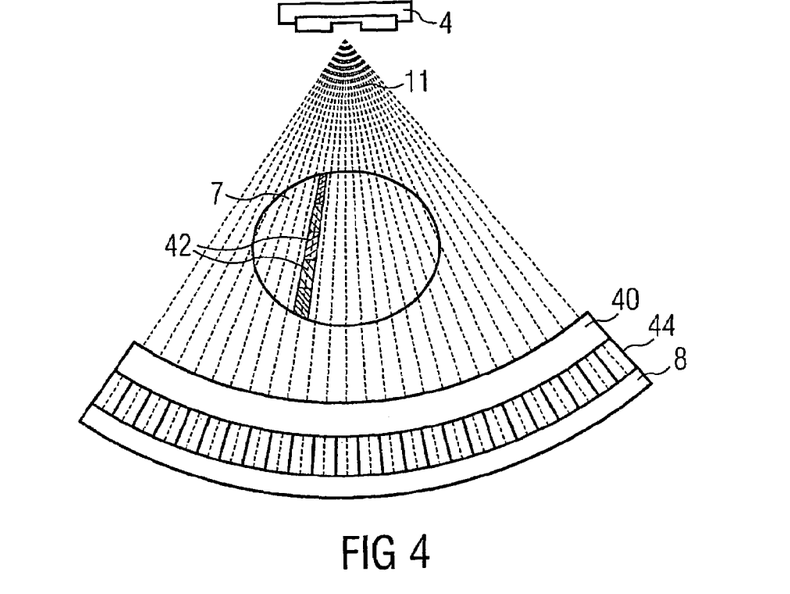
FIG. 4 shows a schematic representation of the source of radiation collimator and detector arrangement of the computer tomography of FIG. 1 in the fan plane.
Figure 5:
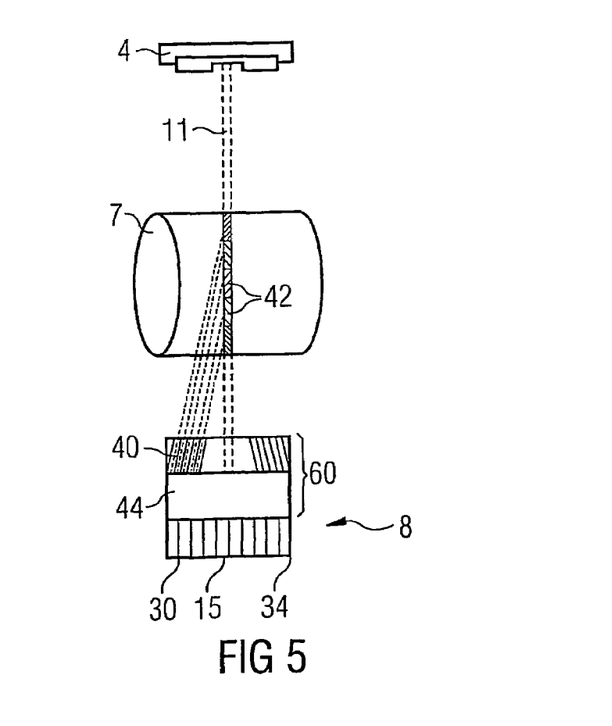
FIG. 5 shows another schematic representation of a side view of the fan plane of an arrangement of the source of radiation, scatter radiation and primary radiation according to an exemplary embodiment of the present invention.

FIGS. 4 and 5 show top (FIG. 4) and cross-sectional (FIG. 5) views of the source of radiation 11, collimator 60 and detector 8 arrangement according to an exemplary embodiment of the present invention as it may be used in a computer tomography apparatus, as, for example, described with reference to FIG. 1.

As may be taken from FIGS. 4 and 5, the energy resolving detector elements 30 are located behind a two-part collimator 60, comprising a first collimator portion (lamellae 40) and a second collimator portion (lamellae 44). A part of the spatial resolution may be achieved by provision of focused lamellae 44 in the second collimator portion. The focused lamellae 44 are focused at the source of radiation 4. Furthermore, the focused lamellae 44 are arranged essentially perpendicular to the fan plane. Due to this, only photons which have been scattered out of the fan plane may be detected by the energy resolving detector elements of detector lines 30 (or 34). Other photons, i.e. photons having another direction are absorbed by the focused lamellae 44 of the second collimator portion.

Thus, photons which are detected by a particular detector element of lines 30 and 34 may therefore only be scattered in a narrow restricted section of the probe. Such regions or sections are indicated by reference numeral 42 in FIGS. 4 and 5.

A further part of the spatial resolution, namely the angular resolution, may be achieved by means of the first collimator portion, comprising further lamellae 40. These further lamellae 40, which are also focused, define a fixed line of vision of a respective energy resolving detector element onto the item of baggage 7. By this, the origin of a photon detected in one particular detector element is restricted to a small portion of the object.

Due to the provision of the first and second collimator portions, i.e. due to the provision of focused lamellae 40 and 44, it may be achieved that only radiation of a fixed angle $\Phi_0$ with respect to the central plane impinges onto the respective energy resolving detector elements. Furthermore, by the arrangement of lamellae 40 and 44, one after another, it may be achieved that each detector element (or each group of detector elements) may only detect scatter radiation from an oblong section 42 of the item of baggage 7. The position, orientation and size of the oblong section 42 may be set by an according arrangement of lamellae 40 and 44.

Instead of the provision of lamellae as first and second collimator portions, the collimator may also be realized by means of a so-called slot-collimator, consisting of, for example, a solid object having a strong absorbance with respect to e.g. x-rays, being provided with focused holes. Behind these focused holes, respective energy resolving detector elements may be provided.

Instead of a solid object, such a slot collimator may also be realized by a plurality of stapled aperture plates. Furthermore, the collimator may be realized by crossing lamellae 40 and 44.

In general, according to an exemplary embodiment of the present invention, the collimator shall be realized such that each detector pixel has only one "line of vision". In the case of the slot collimator being provided with holes, for example along the lines of the detector 8, the lines may be focused onto the source of radiation 4, whereas, along the columns of the detector 8, all holes may be parallel to each other, each defining a constant angle $\Phi_0$ with respect to the central plane.

Preferably, only one detector element is provided for each hole.

As may be taken from FIG. 5, there may also be provided a conventional CT detector, which may, for example, be provided with a one-dimensional or two-dimensional anti-scatter grid, which may also be focused onto the source of radiation 4. The energy resolving detector elements (lines 30 and 34) may be provided on both sides of the primary radiation detector (line 15), which may allow for a higher yield of photons, but may also be provided on one side of the primary radiation detector, which may allow for reduced costs.

As may be taken from FIGS. 4 and 5 in particular, the collimator 60 is provided such that each detector element, in particular of the scatter radiation detector, is only subjected to radiation from a very small predetermined region or section of the item of baggage. Such region or section is determined by an intersection between the illuminated volume and the section of the item of baggage seen by the respective detector cell. Due to this, the energy resolving detector elements of the radiation detector now measure or determine the energy distribution of this region or section of the item of baggage with a fixed angle of incident. Due to this, the scatter distribution may be reconstructed from the readouts of the scatter radiation detector.

In principle, the energy resolving detector elements are located behind a collimator 60, having two portions. One part of the spatial resolution is achieved by means of lamellae 44, focused at the source of radiation. These lamellae 44, as already indicated above, may be arranged essentially perpendicular to the fan plane. Due to the provision of these lamellae 44, only scattered radiation which has been scattered out of the fan plane may impinge on the respective energy resolving detector elements. Thus, only scatter radiation which is generated along a ray may impinge onto the respective column of the detector.

The angular resolution may be achieved by the second set of lamellae, namely lamellae 40. These lamellae are focused at a predetermined section of the object of interest, i.e. the item of baggage 7. Thus, lamellae 40 are arranged such that a predetermined angle of incident is defined with respect to the item of baggage 7. At the same time, this defines which portion of the item of baggage 7 "scatters" onto which detector element.

In other words, due to the provision of lamellae 40 and 44, the scatter radiation detector is only subjected to radiation having a fixed angle and each detector element receives only scattered radiation, which was scattered in a relatively small portion of the item of baggage 7. Such a portion of the item of baggage 7 is indicated by reference numeral 42 in FIGS. 4 and 5.

Advantageously, this may allow that the readout of the scatter radiation detector may directly be used for reconstructing the output image. For this, for example, readouts from a plurality of projections may simply be superimposed for generating the output image. However, for example, the primary radiation measured by lines 15 may be used for correcting the readouts of the scatter radiation detector. For example, an attenuation correction and a primary radiation intensity correction may be applied. Furthermore, the readouts I(E) may be transformed to I(q) and may then be directly back-projected into the volume of the item of baggage 7. I(E) is the measured intensity (number of photons/time interval) at a given energy E. Using $$q = \frac{E}{hc}\sin(\Phi_0/2) \qquad \text{Eq. 1}$$

the intensity distribution can be transformed to I(q) (h: Planck's constant, c: speed of light).

According to another exemplary embodiment of the present invention, the readouts from one projection may be sufficient for determining the scatter distribution of the object of interest, i.e. the item of baggage without reconstruction. However, this may cause that the resolution becomes very anisotropic i.e. very bad in the direction of the fan-rays in the fan plane, better in a direction perpendicular thereto. Furthermore, regions may be covered by strong absorbing objects. However, for this exemplary embodiment of the present invention, no rotating gantry may be required.

For an improved image quality, a rotating gantry may be applied, as will be described in the following with reference to FIG. 6.

Figure 6:
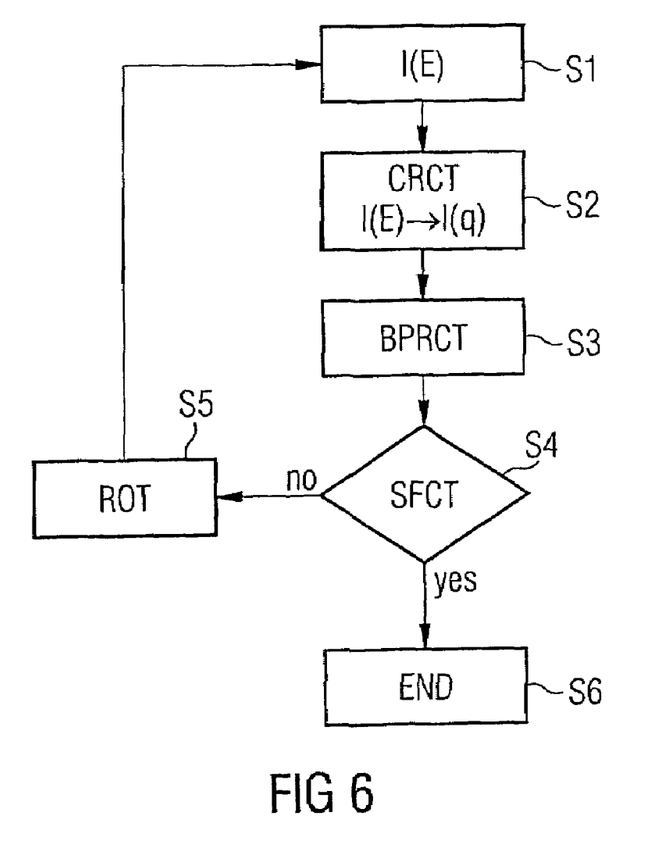
FIG. 6 shows a simplified flow-chart of a method of operating an exemplary embodiment of a computed tomograph according to the present invention.

FIG. 6 shows a simplified flow-chart of a method of operating a computer tomography apparatus according to an exemplary embodiment of the present invention. As indicated by I(E), in step S1 a measurement of a projection may be performed. In other words, in step S1, readouts of the scatter radiation detector and the primary radiation detector are determined for one rotation angle of the gantry. Then, in step S2, a correction of the primary radiation intensity and an attenuation correction may be performed as indicated by CRCT. As indicated by I(E)→I(q) in step S2, a conversion of I(E) to I(q) may be performed by calculating q from E and scatter angle $\Phi_0$ using Eq. 1.

As indicated in subsequent step S3 by BPRCT, a back projection of I(q) into the volume of the item of baggage 7 may be performed in step S3. Then, as indicated in subsequent step S4 by SFCT, it is determined in step S4 whether sufficient projections have been measured or not. The amount of projections required may, for example, be determined by the desired image quality. However, according to an aspect of this method, a preset number of projections may be applied. In case it is determined in step S4 that further projections need to be acquired, the method continues to step S5, where the gantry is rotated by a preset increment. Then, the method continues to step S1.

In case it is determined in step S4 that sufficient projections have been acquired, the method continues to step S6, where it ends.

Due to the use of a plurality of projections for generating the output image in the method described with reference to FIG. 6, a more isotropic resolution and a better statistic of the measurement may be achieved in comparison to the exemplary embodiment, where only one projection is used. Furthermore, advantageously, in comparison to a tomographic reconstructive CSCT, the method and apparatus according to the present invention allows to reduce multiple scattered radiation being brought into the detector, which may allow for an improved quality of the measured scatter spectrum.

Figure 7:
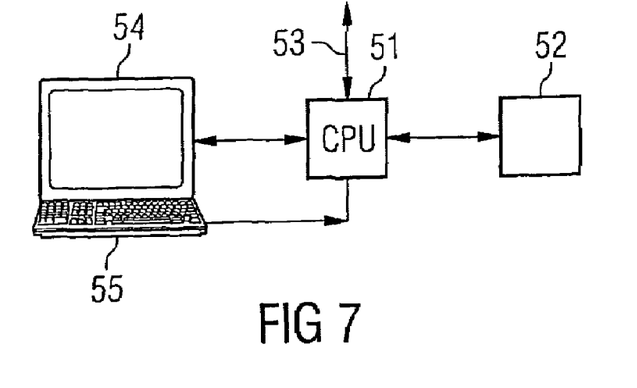
FIG. 7 shows a simplified block diagram of a data processing device according to the present invention.

FIG. 7 shows an exemplary embodiment of a data processing device for performing the method according to the present invention. It should be noted that in spite of the fact that the method of the present invention may also be performed in the calculation unit of a computer tomographic apparatus, it may also be performed in a data processing device such as the one depicted in FIG. 7. For example, the data processing device may be connectable to a computer tomography apparatus. However, it may be sufficient that data acquired by means of a computer tomographic apparatus as described above may be loaded into the memory 52 of the data processing device depicted in FIG. 7.

As may be taken from FIG. 7, a central processing unit (CPU) or image processor 51 is connected to the memory 52 for storing readouts from the detectors or the output image. As indicated before, the data may be acquired by a CSCT scanner, such as depicted in FIG. 1. The image processor 51 may be furthermore connected to a plurality of input/output-network or other diagnosis devices. The image processor 51 is furthermore connected to a display 54 (for example to a computer monitor) for displaying information or image computed or adapted in the image processor 51. An operator may interact with the image processor 51 via a keyboard 55 and/or other output devices, which are not depicted in FIG. 7.

As indicated above, the present invention may be applied not only to baggage inspection, but may also be applied to medical applications or material testing and material science. An improved image quality and a reduced amount of calculations required may be achieved.

It should be noted that "comprising" does not exclude other elements or steps and "a" or "an" does not exclude a plurality, and that a single processor or other unit may fulfill the function of several means recited in the claims. Any means, feature or step described with reference to one of the above embodiments may also be applied in combination with any other means, feature or step described with reference to another one of the above embodiments. Also, any reference signs in the claims shall not be construed as limiting the scope.

The invention claimed is:

1. A computer tomography apparatus for examination of an object of interest, the computer tomography apparatus comprising:
    a source of radiation;
    a scatter radiation detector for receiving a scatter radiation scattered by the object of interest, said detector being arranged opposite to the source of radiation with an offset with respect to a fan plane which extends through the object of interest and the source of radiation; and
    a first collimator comprised of:
        a second collimator focused at the source of radiation; and
        a third collimator focused at the section of the object of interest;
    wherein the scatter radiation detector has a plurality of detector regions organized substantially as a detector matrix comprised of matrix elements defined by horizontal and vertical detector lines, each of the plurality of detector regions having at least one energy resolving detector element;
    wherein the first collimator is adapted such that radiation impinging on the at least one energy resolving detector element of a respective region of the plurality of regions is substantially restricted to scatter radiation scattered from a predetermined section of the object of interest, the dimensions of which correspond substantially to a matrix element of said detector matrix;
    wherein the source of radiation is adapted such that a fan beam of radiation is applied to the object of interest in the fan plane.

2. The computer tomography apparatus of claim 1, wherein the second and third collimators are arranged one after another with respect to the source of radiation.

3. The computer tomography apparatus of claim 1,
wherein the second collimator has first lamellae which are focused at the source of radiation and are arranged substantially perpendicular to the fan plane such that radiation impinging on the at least one first detector element in the region of the plurality of regions associated with the second collimator is restricted to radiation having a first predetermined angle with respect to the source of radiation; and
wherein the third collimator has second lamellae which are focused at the section of the object of interest such that radiation impinging on the at least one first detector element in the region of the plurality of regions associated with the third collimator is restricted to radiation having a second predetermined angle with respect to the section of the object of interest.

4. The computer tomography apparatus of claim 1, wherein the second and third collimators are together implemented by means of a slot collimator comprising holes which, for each respective region, are respectively focused in the fan-plane at the source of radiation and out of the fan-plane defines a fixed scatter angle and a section within the section of the object of interest from which radiation can reach a detector element.

5. The computer tomography apparatus of claim 1, further comprising:
a primary radiation detector;
wherein the primary radiation detector is arranged opposite to the source of radiation in the fan plane for receiving a primary radiation attenuated by the object of interest.

6. The computer tomography apparatus of claim 5, wherein the at least one energy resolving detector element is a direct-converting semiconductor cell; and
wherein the primary radiation detector comprises scintillator cells.

7. The computer tomography apparatus of claim 1, further comprising a calculation unit;
wherein the calculation unit is adapted to generate a first output image without performing a reconstruction.

8. The computer tomography apparatus of claim 7, wherein the calculation unit is further adapted to generate the first output image by superposing second images corresponding to readouts of the scatter radiation detector obtained from different viewing angles with respect to the object of interest.

9. The computer tomography apparatus of claim 7, wherein the calculation unit is further adapted to perform at least one of an attenuation correction and a primary radiation intensity correction.

10. A computer tomography apparatus for determining a first output image by using readouts from a scatter radiation detector, the computer tomography apparatus having:
a source of radiation;
a scatter radiation detector for receiving a scatter radiation scattered by the object of interest wherein the scatter radiation detector has a plurality of detector regions organized substantially as a detector matrix comprised of matrix elements defined by horizontal and vertical detector lines;
wherein each of the plurality of detector regions has at least one energy resolving detector element;
a first collimator comprised of a second collimator focused at the source of radiation and a third collimator focused at a section of the object of interest;
wherein the first collimator is adapted such that radiation impinging on the at least one energy resolving detector element of a respective region of the plurality of regions is substantially restricted to scatter radiation scattered from a predetermined section of the object of interest, the dimensions of which correspond substantially to a matrix element of said detector matrix;
wherein the scatter radiation detector is arranged opposite to the source of radiation with an offset with respect to a fan plane;
wherein the fan plane extends through the object of interest and the source of radiation;
wherein the scatter radiation detector has a plurality of regions;
wherein each of the regions has at least one first detector element;
wherein the at least one first detector element is an energy resolving detector element;
wherein the first collimator is adapted such that scatter radiation impinging on the at least one first detector element of a respective region of the plurality of regions is substantially restricted to radiation scattered from a predetermined section of the object of interest; and
wherein the source of radiation is adapted such that a fan beam of radiation is applied to the object of interest in the fan plane; and
a data processing device comprising:
a memory for storing the readouts from the scatter radiation detector; and
a processor which is adapted to perform at least the following operation: generating a first output image from the readouts without performing a reconstruction.

11. The data processing device of claim 10, wherein the processor is further adapted to generate the first output image by superposing second images corresponding to readouts of the radiation detector obtained from different viewing angles with respect to the object of interest.

12. The data processing device of claim 10, wherein the processor is further adapted to perform at least one of an attenuation correction and a primary radiation intensity correction.

13. A method of performing a fan-beam coherent scatter computer tomography scan with a computer tomography apparatus for examination of an object of interest, the method comprising the steps of:
providing a source of radiation;
providing a scatter radiation detector for receiving a scatter radiation scattered by the object of interest, wherein the scatter radiation detector has a plurality of detector regions organized substantially as a detector matrix comprised of matrix elements defined by horizontal and vertical detector lines;
providing a first collimator comprised of a second collimator focused at the source of radiation and a third collimator focused at a section of the object of interest, wherein the first collimator is adapted such that radiation impinging on the at least one energy resolving detector element of a respective region of the plurality of regions is substantially restricted to scatter radiation scattered from a predetermined section of the object of interest, the dimensions of which correspond substantially to a matrix element of said detector matrix;
energizing the source of radiation to generate a fan beam of radiation;
determining readouts from the scatter radiation detector;
generating a first output image from the readouts by superimposing images without performing a reconstruction.

14. The method of claim 13, wherein the step of generating a first output image from the readouts without performing a reconstruction further comprises the steps of: superposing second images corresponding to readouts of the radiation detector obtained from different viewing angles with respect to the object of interest; andperforming at least one of an attenuation correction and a primary radiation intensity correction.

15. The method of claim 14, further comprising the steps of:
   determining attenuation coefficients of the object of interest by using readouts of a primary radiation detector arranged in the fan plane;
   determining parameters for the absorption correction of the readouts from the scatter radiation detector on the basis of the attenuation coefficients.

16. The method of claim 13, wherein the source of radiation is operated such that the primary radiation detector and the scatter radiation detector are subjected to the fan beam radiation emitted from the source of radiation essentially at the same time.

17. The method of claim 13, wherein the scatter radiation detector is arranged opposite to the source of radiation with an offset with respect to a fan plane.

18. The method of claim 13, wherein the fan plane extends through the object of interest and the source of radiation.

19. The method of claim 13, wherein the scatter radiation detector has a plurality regions.

20. The method of claim 13, wherein each of the regions has at least one first detector element.

21. The method of claim 13, wherein the at least one first detector element is an energy resolving detector element.

22. The method of claim 13, wherein the first collimator is adapted such that radiation impinging on the at least one first detector element of a respective region of the plurality of regions is substantially restricted to scatter radiation scattered from a predetermined section of the object of interest.

23. The method of claim 13, wherein the source of radiation is adapted such that a fan beam of radiation is applied to the object of interest in the fan plane.

* * * * *